US009147014B2

(12) United States Patent
Lastra

(10) Patent No.: US 9,147,014 B2
(45) Date of Patent: Sep. 29, 2015

(54) SYSTEM AND METHOD FOR IMAGE SELECTION OF BUNDLED OBJECTS

(75) Inventor: Raúl Andrés Lastra, Santiago (CL)

(73) Assignee: WOODTECH MEASUREMENT SOLUTIONS, Las Condes, Santiago (CL)

(*) Notice: Subject to any disclaimer, the term of this patent is extended or adjusted under 35 U.S.C. 154(b) by 527 days.

(21) Appl. No.: 13/601,290

(22) Filed: Aug. 31, 2012

(65) Prior Publication Data
US 2013/0141568 A1 Jun. 6, 2013

Related U.S. Application Data

(60) Provisional application No. 61/529,603, filed on Aug. 31, 2011, provisional application No. 61/529,549, filed on Aug. 31, 2011.

(51) Int. Cl.
H04N 7/18 (2006.01)
G06F 17/50 (2006.01)
G06T 7/60 (2006.01)
G01B 11/24 (2006.01)
G01N 21/898 (2006.01)
G01N 33/18 (2006.01)

(52) U.S. Cl.
CPC ............... *G06F 17/50* (2013.01); *G01B 11/24* (2013.01); *G01N 21/8986* (2013.01); *G01N 33/1826* (2013.01); *G06T 7/60* (2013.01); *G01N 33/18* (2013.01)

(58) Field of Classification Search
CPC .... G06F 17/50; G01N 21/8986; G01N 33/18; G01N 33/1826; G01B 11/24; G06T 7/60
USPC ........ 348/125, 135, 86, 91, 92; 356/625, 627, 356/634, 635, 237.1, 909; 382/141, 206, 382/224, 225; 702/128, 155, 179; 144/335, 144/356, 402, 403
See application file for complete search history.

(56) References Cited

U.S. PATENT DOCUMENTS

| | | | |
|---|---|---|---|
| 3,513,321 A | 5/1970 | Sherman |
| 3,565,531 A | 2/1971 | Kane et al. |
| 3,593,632 A | 7/1971 | Woodruff |
| 3,619,070 A | 11/1971 | Pirlet |
| 3,802,774 A | 4/1974 | Eschler et al. |

(Continued)

FOREIGN PATENT DOCUMENTS

| | | |
|---|---|---|
| CA | 2306094 C | 2/2002 |
| CN | 201233223 | 5/2009 |

(Continued)

*Primary Examiner* — Victor Kostak
(74) *Attorney, Agent, or Firm* — Goodwin Procter LLP

(57) ABSTRACT

A bundled object image selection system includes an array of sensors configured to at least partially surround a bundle of objects, wherein the sensors are lasers adapted to obtain physical dimensional data about the bundle. The system also includes at least one camera configured to obtain a plurality of images of the bundle, a processor for executing computer-executable instructions, and a memory for storing computer executable instructions. When the instructions are executed, the processor implements a limit module that processes the physical dimensional data to determine a limit of the bundle and a selection module that selects at least one image from the plurality of images corresponding to the limit.

20 Claims, 18 Drawing Sheets

(56) References Cited

U.S. PATENT DOCUMENTS

| | | | |
|---|---|---|---|
| 3,976,384 A | 8/1976 | Matthews et al. | |
| 4,122,525 A | 10/1978 | Eaton | |
| 4,122,957 A | 10/1978 | Allen et al. | |
| 4,364,732 A | 12/1982 | Chi et al. | |
| 4,375,921 A | 3/1983 | Morander | |
| 4,392,204 A | 7/1983 | Prim et al. | |
| 4,528,651 A | 7/1985 | Brock et al. | |
| 4,687,107 A | 8/1987 | Brown et al. | |
| 4,762,990 A | 8/1988 | Caswell et al. | |
| 4,879,752 A | 11/1989 | Aune et al. | |
| 4,893,346 A | 1/1990 | Bishop | |
| 4,913,551 A | 4/1990 | Davis | |
| 4,984,172 A | 1/1991 | Luminari | |
| 5,088,827 A | 2/1992 | Kyriakis | |
| 5,257,101 A * | 10/1993 | Lee | 348/95 |
| 5,267,018 A | 11/1993 | Kauppinen | |
| 5,394,342 A * | 2/1995 | Poon | 702/137 |
| 5,456,119 A | 10/1995 | Nakazaki et al. | |
| 5,544,757 A | 8/1996 | Geiger et al. | |
| 5,614,710 A | 3/1997 | Mondie et al. | |
| 5,703,960 A | 12/1997 | Soest | |
| 5,815,274 A | 9/1998 | Dlugos | |
| 5,892,808 A * | 4/1999 | Goulding et al. | 378/63 |
| 5,900,590 A | 5/1999 | Solberg, Jr. et al. | |
| 5,930,734 A | 7/1999 | Hofmann et al. | |
| 5,953,127 A | 9/1999 | Washio et al. | |
| 5,960,104 A | 9/1999 | Conners et al. | |
| 6,031,567 A * | 2/2000 | Johnson | 348/91 |
| 6,163,591 A | 12/2000 | Benjamin | |
| 6,181,411 B1 | 1/2001 | Harris et al. | |
| 6,182,725 B1 | 2/2001 | Sorvik | |
| 6,407,819 B1 | 6/2002 | Kuratle | |
| 6,480,290 B1 | 11/2002 | Singh et al. | |
| 6,598,477 B2 | 7/2003 | Floyd | |
| 6,756,789 B1 | 6/2004 | Parker et al. | |
| 6,847,740 B1 | 1/2005 | Birkle | |
| 6,951,988 B2 | 10/2005 | Falcou et al. | |
| 6,958,465 B2 | 10/2005 | Haberer et al. | |
| 6,996,497 B2 | 2/2006 | Floyd et al. | |
| 7,098,435 B2 | 8/2006 | Mueller et al. | |
| 7,146,276 B2 | 12/2006 | Smith et al. | |
| 7,161,688 B1 | 1/2007 | Bonner et al. | |
| 7,415,491 B2 | 8/2008 | Sekiguchi | |
| 7,526,064 B2 | 4/2009 | Akery | |
| 7,660,433 B2 | 2/2010 | Dralle et al. | |
| 7,660,665 B2 | 2/2010 | Tamamoto et al. | |
| 7,684,590 B2 | 3/2010 | Kampchen et al. | |
| 7,978,192 B2 | 7/2011 | Elsberg et al. | |
| 8,115,928 B2 | 2/2012 | Johnson et al. | |
| 8,134,717 B2 | 3/2012 | Pangrazio et al. | |
| 8,155,426 B2 * | 4/2012 | Paavola | 382/141 |
| 2002/0024677 A1 | 2/2002 | Metcalfe et al. | |
| 2005/0147286 A1 | 7/2005 | Lee et al. | |
| 2005/0190958 A1 * | 9/2005 | Woods et al. | 382/141 |
| 2007/0286474 A1 | 12/2007 | Dralle | |
| 2008/0208828 A1 | 8/2008 | Boiman et al. | |
| 2010/0071222 A1 | 3/2010 | Solomon et al. | |
| 2010/0141754 A1 * | 6/2010 | Hiraoka | 348/93 |
| 2010/0228500 A1 | 9/2010 | Giudiceandrea et al. | |
| 2010/0290691 A1 * | 11/2010 | Eilbert et al. | 382/132 |
| 2011/0193711 A1 | 8/2011 | Faugier et al. | |
| 2011/0235065 A1 | 9/2011 | Wilson et al. | |
| 2011/0246073 A1 * | 10/2011 | Ma | 702/2 |
| 2011/0320139 A1 | 12/2011 | Amir et al. | |
| 2012/0092461 A1 | 4/2012 | Fisker et al. | |

FOREIGN PATENT DOCUMENTS

| | | |
|---|---|---|
| EP | 1061361 A1 | 12/2000 |
| EP | 1526377 A1 | 4/2005 |
| JP | 08-133449 | 5/1996 |
| SU | 01411209 A1 | 7/1988 |
| WO | WO-9105245 A1 | 4/1991 |
| WO | WO-9322659 A1 | 11/1993 |
| WO | WO-02091286 A2 | 11/2002 |
| WO | WO-2006117650 A1 | 11/2006 |
| WO | WO-2009123628 A1 | 10/2009 |
| WO | WO-2012084708 A1 | 6/2012 |
| WO | WO-2012089185 A1 | 7/2012 |

* cited by examiner

US 9,147,014 B2

SYSTEM AND METHOD FOR IMAGE SELECTION OF BUNDLED OBJECTS

CROSS-REFERENCE TO RELATED APPLICATIONS

This application claims priority to U.S. provisional patent application Ser. Nos. 61/529,549 and 61/529,603, both filed on Aug. 31, 2011, each of which is hereby incorporated by reference in its entirety.

TECHNICAL FIELD

This invention relates to systems and methods for detecting distinguishing characteristics in a bundle of objects, and more specifically, to automatic log scaling and the detection of defects in a bundle of logs. This invention also relates to systems and methods for selecting images of a bundle of objects, and more specifically, to identifying limits of a bundle and associating images therewith.

BACKGROUND INFORMATION

Wood processing mills all over the world convert some form of forest raw material (e.g., wood logs, chips, sawdust, biomass) into a finished product (e.g., wood pulp, paper, timber, fiber boards, energy). In most cases, these raw materials arrive at the mill on some form of vehicle—typically trucks, but also trains and water vessels. Most of the time it is important to measure the quantity (and perhaps other parameters) of these raw materials as they arrive at the mill, including for payment, inventory, accounting and/or other purposes.

To determine the quantity of raw material in a given delivery, various methods can be used, primarily relating to either weight or volume. Weight measurement is typically used for its convenience and simplicity, but has a significant limitation when the density of the measured material is uncertain. For example, forest raw materials can have greatly variable densities not only due to their biological composition, but also due to the varying degree of moisture they hold. A freshly cut log can have twice the moisture content of one that has been drying for six weeks. Volumetric measurement removes the problem of variable density from the equation, but it can be very difficult to measure the volume of highly heterogeneous materials that arrive at wood processing mills in an automatic and repeatable manner.

In the lumber industry, large diameter logs (typically about 7-30 inches) often arrive at a saw mill loaded on trucks (or other vehicles) and are then sawn and processed into finished lumber. In the Southeast United States, which has a significant amount of the country's lumber industry, logs are usually delivered by logging trucks and are weight-scaled at the mill gate. Some mills include additional controls, such as counting logs and looking for "defects," that are usually done visually by an on-site operator. Visual inspection typically requires the operator to walk around the truck looking for different defects, sometimes having to climb onto the truck to gain better visual access to some logs. This represents a safety hazard and can consume quite a bit of time, during which the truck remains stationary. Some mills choose (or are required by law) to hire large teams of human scalers that select random trucks to be hand-scaled, log-by-log, in a meticulous and time-consuming process that involves unloading every log to the ground. All these processes are constrained by time and cost. Furthermore, the additional movement of logs (from truck to ground and ground to log yard) adds machinery cost, requires large amounts of space in the mill, and increases log breakage due to additional log handling.

Sawmills are usually most interested in the total useful volume of a given log (often measured in "cubic board feet"), since this indicates how much finished lumber can be produced from that log. Weight alone is often an incomplete variable, since weight for a given volume can vary significantly depending on density and moisture content. Furthermore, sawmills tend to assign higher value to larger diameter logs as higher value-added products can be made from these (e.g., a high diameter log allows for the production of many combinations of different products, whereas small diameter logs can only be used to produce small products). Sawmills may also penalize for defects in logs that take away from the useful volume, such as crookedness, cracks, splits, rot, knots and others.

Accordingly, there is a need for a system that automatically and precisely estimates desired variables of loads delivered to a mill to improve the efficiency of the mill by a significant margin in terms of time and cost. There is also a need for a system that aids a human operator in rapidly detecting and registering specific log defects in a much more time and cost efficient manner, thus increasing the mill's capability of searching for defects and/or reducing the need for additional people. It is also desirable that this system provides the capability of storing images of each load that is scanned, as well as the inputs of the human operator.

SUMMARY OF THE INVENTION

In general and in one aspect, a bundled object variability detection system is provided. The system includes an array of sensors at least partially surrounding a bundle of objects, wherein the sensors are lasers for obtaining physical dimensional data about the bundle. The system also includes a processor for executing computer-executable instructions and a memory for storing computer executable instructions. When the instructions are executed, the processor implements a first module that receives the physical dimensional data from the sensors, a second module that locates a distinct cross-section of a singular object within the bundle based on the physical dimensional data, a third module that determines a model of the singular object based on the located cross-section of the singular object, and a fourth module that analyzes the model to determine if the individual object embodies one or more distinguishing characteristics.

In some embodiments, the sensors are disposed on three sides of the bundle. In some embodiments, the objects are logs. In some embodiments, the physical dimensional data comprises peripheral data. In some embodiments, the second module is adapted to apply a curve fitting technique to determine a shape (which may be a circle) that fits the cross-section, and the curve fitting technique may be a local circle fitting. In some embodiments, the second module further determines an estimated detectable portion of the singular object, compares the estimated detectable portion to the physical dimensional data associated with the object, and determines an occlusion factor based on the comparison. In some embodiments, the second module further determines an intersection of the singular object with another object in the bundle. In some embodiments, the model is a three-dimensional model. In some embodiments, the distinguishing characteristics are a large end diameter, a small end diameter, a length, and/or a curvature.

In general, in another aspect, a method for detecting variability in individual objects in a bundle of objects includes obtaining physical dimensional data related to a bundle of objects using laser sensors and processing the physical dimensional data with a processor for executing computer-executable instructions. Processing includes locating a cross-section of an individual object, creating a model of the individual object based on the located cross-section, and analyzing the model to determine if the individual object embodies one or more distinguishing characteristics.

In some embodiments, the obtaining step occurs when the objects are in relative motion to the laser sensors. In some embodiments, the laser sensors are located on three sides of the bundle. In some embodiments, the objects are logs. In some embodiments, the physical dimensional data is peripheral data. In some embodiments, the locating step includes applying a curve fitting technique to determine a shape (which may be a circle) that fits the cross-section, and the curve fitting technique may be a local circle fitting. In some embodiments, the locating step includes determining an estimated detectable portion of the singular object, comparing the estimated detectable portion to the physical dimensional data associated with the object, and determining an occlusion factor based on the comparison. In some embodiments, the locating step includes determining an intersection of the singular object with another object in the bundle. In some embodiments, the model is a three-dimensional model. In some embodiments, the distinguishing characteristics are a large end diameter, a small end diameter, a length, and/or a curvature.

In general, in another aspect, a bundled object image selection system includes an array of sensors configured to at least partially surround a bundle of objects, wherein the sensors are lasers adapted to obtain physical dimensional data about the bundle. The system also includes at least one camera configured to obtain a plurality of images of the bundle, a processor for executing computer-executable instructions, and a memory for storing computer executable instructions. When the instructions are executed, the processor implements a limit module that processes the physical dimensional data to determine a limit of the bundle and a selection module that selects at least one image from the plurality of images corresponding to the limit.

In some embodiments, the sensors are laser sensors. In some embodiments, the sensors are located on at least three sides of the bundle. In some embodiments, the objects are logs. In some embodiments, the physical dimensional data includes distance and angle data between a plurality of set points. In some embodiments the camera is configured to take at least one of photographs and video. In some embodiments, the limit module processes histogram vectors starting at a center of the bundle and working outwards. In some embodiments, the selected image depicts an end of the bundle. In some embodiments, the method includes a cross-section module that organizes the physical dimensional data into a plurality of cross-sections of the bundle. In some embodiments, the system includes a timing module that associates the physical dimensional data with at least one image. In some embodiments, the system includes a synchronization mechanism, and the synchronization mechanism may be configured to use electrical signals to trigger the start of the sensors and the at least one camera.

In general, in another aspect, a method for selecting an image of bundled objects includes obtaining physical dimensional data about the bundled objects using laser sensors, recording a plurality of images of the bundled objects with at least one camera, processing the physical dimensional data with a processor to determine a limit of the bundle, and selecting at least one image from the plurality of images corresponding to the limit.

In some embodiments, the obtaining step occurs when the objects are in relative motion to the laser sensors. In some embodiments, the sensors are laser sensors. In some embodiments, the sensors are located on at least three sides of the bundle. In some embodiments, the objects are logs. In some embodiments, the physical dimensional data is distance and angle data between a plurality of set points. In some embodiments, the recording step includes taking one of photographs and video. In some embodiments, the processing step includes processing histogram vectors starting at a center of the bundle and working outwards. In some embodiments, the selected image depicts an end of the bundle. In some embodiments, the method includes the step of organizing the physical dimensional data into a plurality of cross-sections of the bundle. In some embodiments, the method includes the step of associating the physical dimensional data and the at least one image with a common time indicator. In some embodiments, the method includes synchronizing the start of the sensors and the at least one camera with an electrical signal.

Other aspects and advantages of the invention will become apparent from the following drawings, detailed description, and claims, all of which illustrate the principles of the invention, by way of example only.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1A:
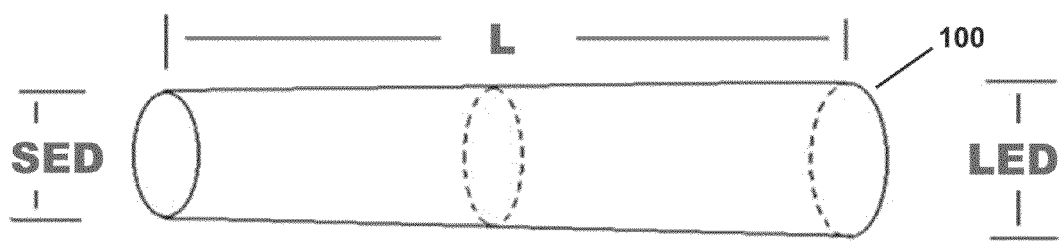
FIGS. 1A to 1E are depictions of various distinguishing characteristics of logs according to an embodiment of the invention.
Figure 1B:
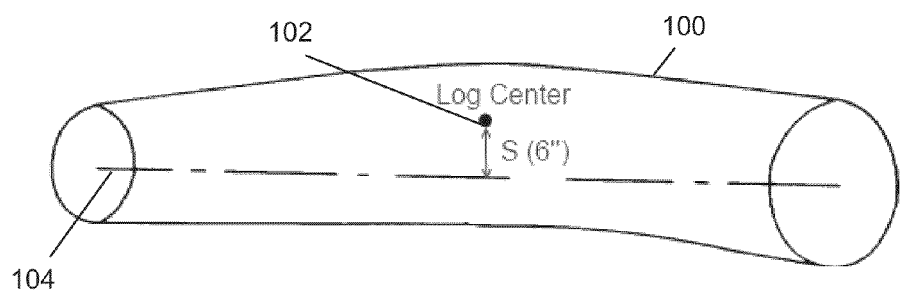

In the forestry industry, logs can be used for a variety of purposes (e.g., lumber, pulp and paper, fiberboard, etc.). Depending on the intended use of the logs, different distinguishing characteristics of the logs may be of interest, particularly those distinguishing characteristics considered to be defects in the logs. Examples of distinguishing characteristics are depicted in FIGS. 1A to 1E. FIG. 1A depicts a log 100 with a length ("L"), a small end diameter ("SED"), and a large end diameter ("LED"). The log 100 may be considered to have a defect if the length, the small end diameter, and/or the large end diameter fall outside of an acceptable range. The acceptable range may be defined by any interested party, such as mill operators. FIG. 1B depicts the log 100 with a curvature (also known as "crook" or "sweep"), as defined by a distance (or curvature index) "S" between the log center 102 at a point along the length of the log 100 and an axis 104 defined between the centers of the ends of the log 100. The log 100 may be deemed to have a defect of being too crooked if the curvature index is outside of a specified range.

Figure 1C:
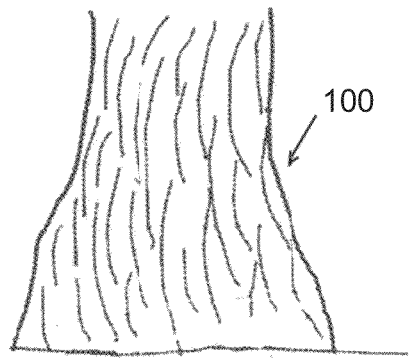
Figure 1D:
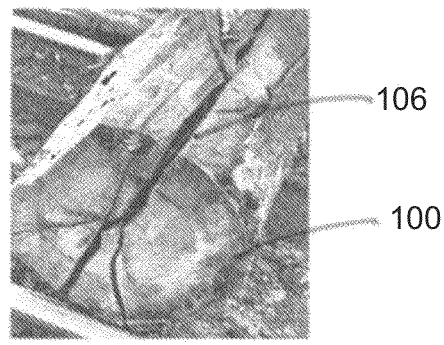
Figure 1E:
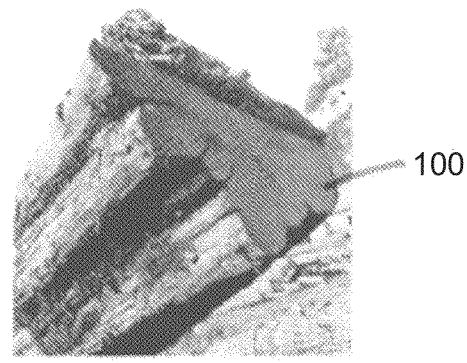

While the above described distinguishing characteristics may be detected automatically, other distinguishing characteristics may be better suited for visual detection. FIG. 1C depicts butt swell in the log 100, which may be defined as expansion in the lower end of the tree trunk above and beyond the usual stump flare found in all species. This is often considered undesirable as the wood in the swollen part of the log 100 is usually too soft to be useful for many applications, such as construction or veneer logs. FIG. 1D depicts the log 100 with a split 106, which is a crack that extends longitudinally into the log 100, thereby decreasing the total useful volume of the log 100. FIG. 1E depicts the log 100 with an uneven butt, which occurs when a cross section of the lower end of the log 100 is highly uneven (i.e., not circular), again decreasing the total useful volume of the log 100. A comprehensive description of log defects and the treatment they are given can be found in the U.S. Forest Service and USDA "National Forest Log Scaling Handbook."

Figure 2:
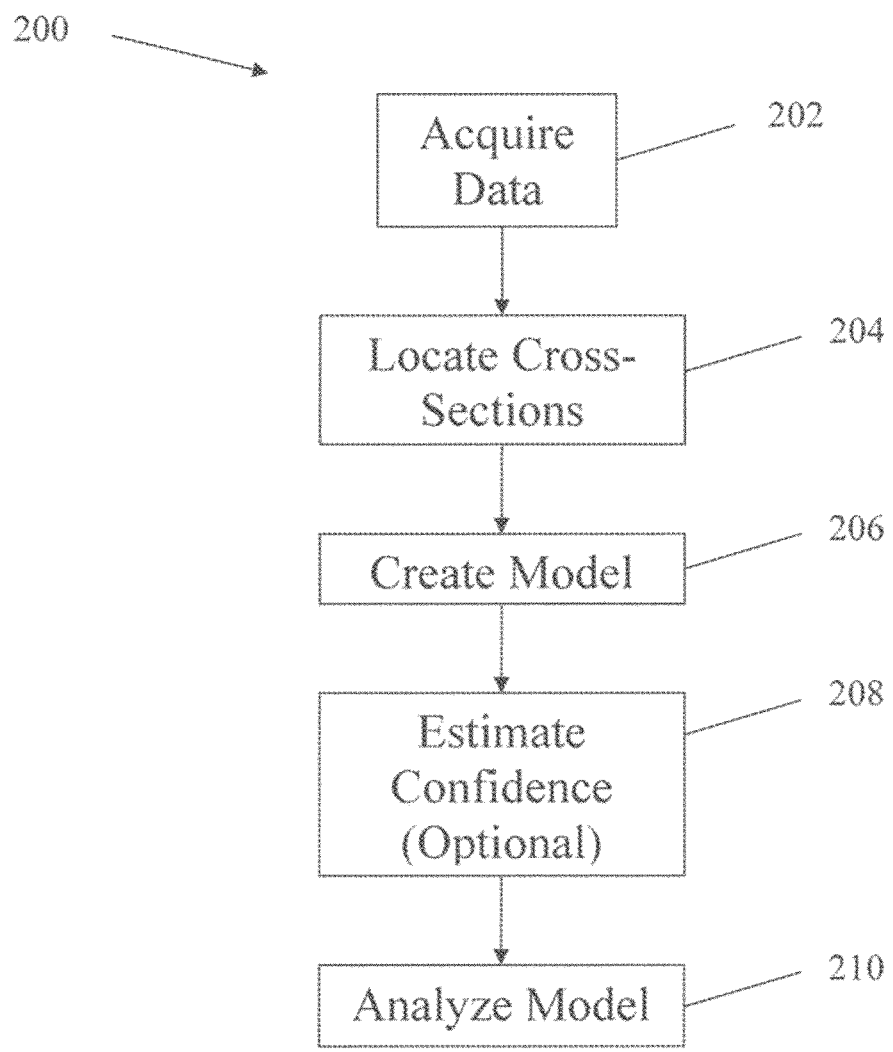
FIG. 2 is a block diagram illustrating by example a process for detecting variability in bundled objects according to an embodiment of the invention.

FIG. 2 depicts a process 200 for detecting variability in individual objects in a bundle of objects, where the variability to be detected may be defined by a user as one or more distinguishing characteristics, as set forth above. The process 200 includes acquiring/obtaining physical dimensional data related to the bundle of objects (e.g., by using laser sensors) (Step 202) and processing the physical dimensional data with a processor for executing computer-executable instructions. Processing may include locating a cross-section of an individual object (Step 204), creating a model of the individual object based on the located cross-section (Step 206), optionally estimating confidence in the model (Step 208), and analyzing the model to determine if the individual object embodies one or more distinguishing characteristics (Step 210).

Figure 3:
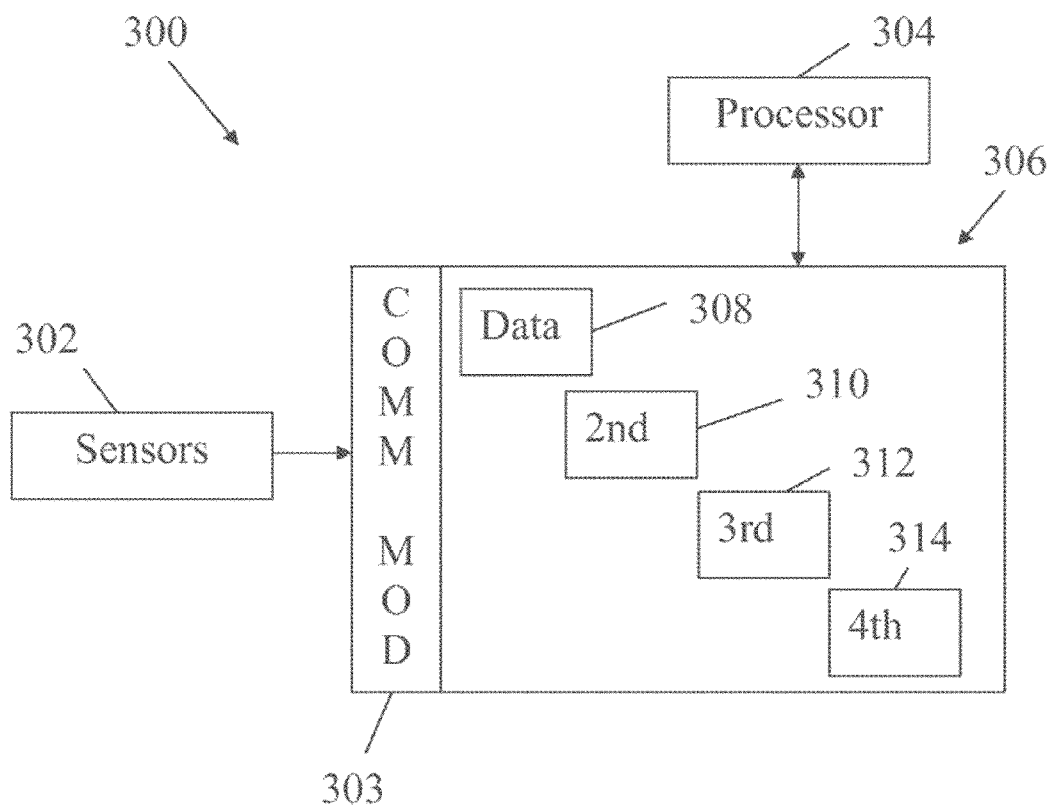
FIG. 3 is a block diagram illustrating by example a system for detecting variability in bundled objects according to an embodiment of the invention.

FIG. 3 is a physical depiction of a bundled object variability detection system 300, including an array of sensors 302 (e.g., laser sensors) that at least partially surround the bundle of objects. The sensors 302 are adapted to obtain physical dimensional data about the bundle and communicate the data through a communication module 303 to a subsystem/memory 306 for storing the computer-executable instructions. The system 300 also includes a processor 304 for executing the computer-executable instructions. The memory 306 includes a first module 308 that receives the physical dimensional data from the sensors 302, a second module 310 that locates a distinct cross-section of a singular object within the bundle based on the physical dimensional data, a third module 312 that determines a model of the singular object based on the located cross-section of the singular object, and a fourth module 314 that analyzes the model to determine if the individual object embodies one or more distinguishing characteristics. The memory 306 may also include a fifth module to determine a confidence value in the model.

Figure 4A:
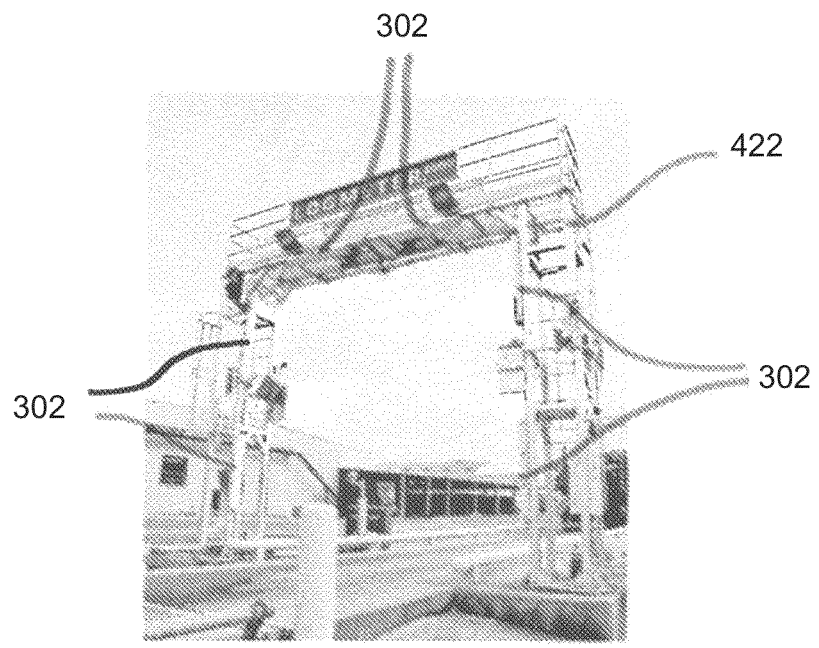
FIGS. 4A and 4B depict an array of sensors according to an embodiment of the invention.
Figure 6:
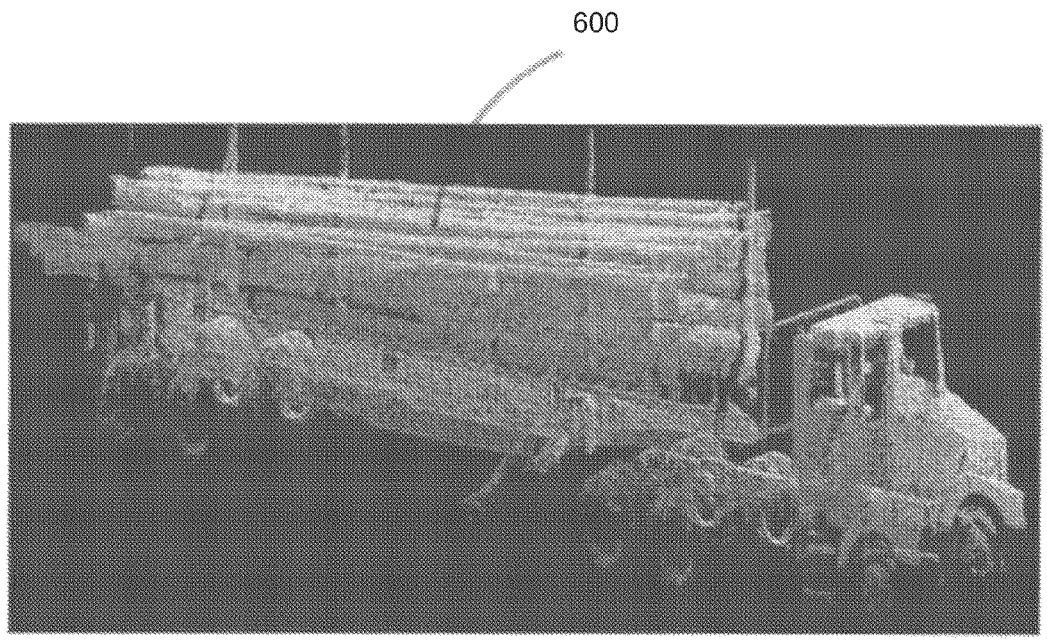
FIGS. 6 and 7 depict images of bundle data as obtained by the sensors according to an embodiment of the invention.

One embodiment of the sensor array 302 is shown in FIG. 4A. The depicted array 302 is a Logmeter® 4000 system available from Woodtech Measurement Solutions (Santiago, Chile) having individual laser-scanning sensors 302 on a rigid structure 422 (e.g., a metallic structure) for acquiring at least physical dimensional data about the objects (e.g., logs). The structure 422 is sized for a logging truck to be able to drive through it with sufficient clearance on all sides. The sensors 302 may be disposed on multiple sides of the structure 422, such that when a truck drives through with a bundle 600 (or multiple bundles 600) of logs 100, as depicted in FIG. 6, the sensors 302 are recording data about the bundle 600 from multiple sides (e.g., from three sides). In some embodiments, the sensors 302 may acquire data on the bundle 600 from fewer than three sides, and the sensors 302 may be disposed on the ground to acquire data from beneath the bundle 600. Additional equipment may be added to the structure 422, such as one or more cameras.

Figure 4B:
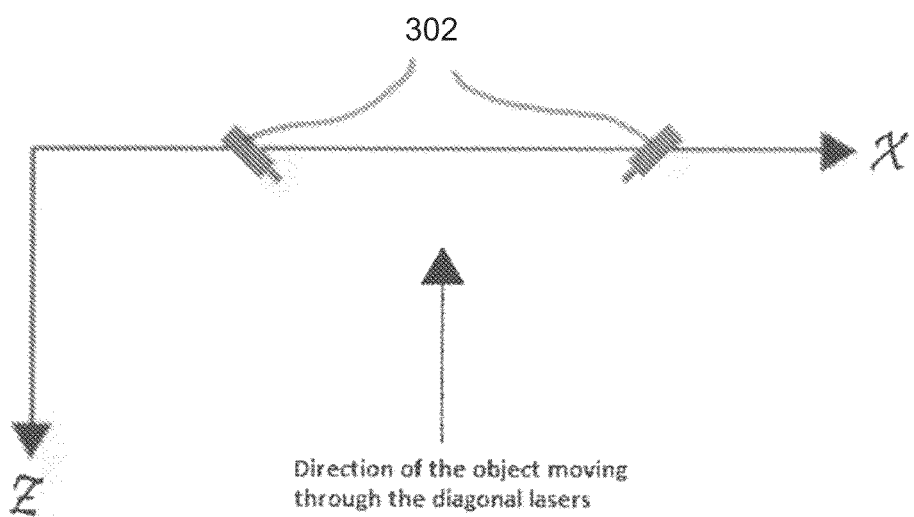
Figure 5:
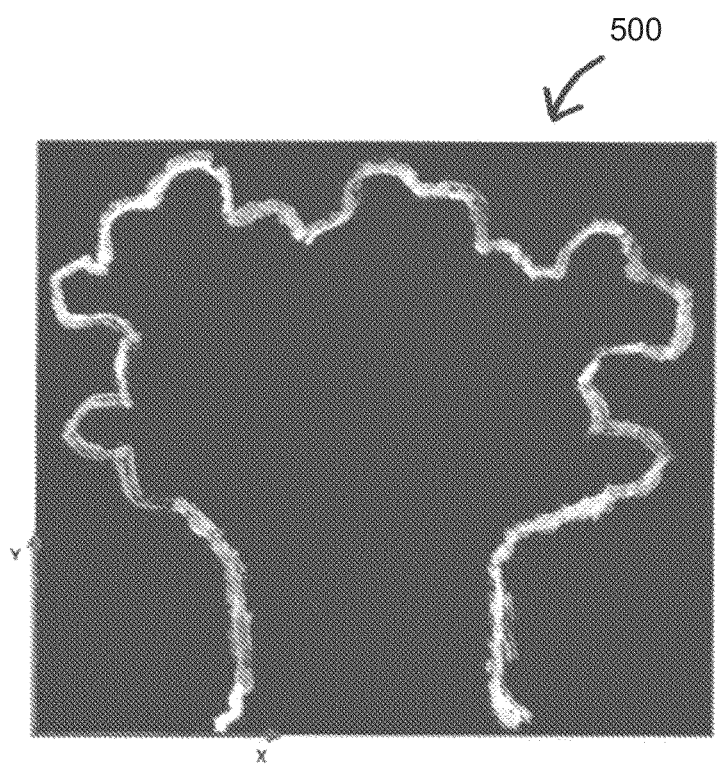
FIG. 5 depicts a cross-section of a bundle detected by sensors according to an embodiment of the invention.

The sensors 302 may precisely measure the distance and angle of a set number of points in its field of vision. The number of points depends on the laser resolution and the laser capture angles. By placing an array of lasers 302 to cover the same plane (perpendicular to the trajectory of the objects) from different positions, a complete cross-section 500 or scan of the bundle 600 may be obtained, as shown in FIG. 5. FIG. 4B depicts additional sensors 302 that may be disposed at angles relative to the trajectory of the objects at the measured data point to obtain additional data, including data on a face at a limit of the bundle 600 to acquire data about all (or substantially all) of the logs 100. The laser array 302 may be configured to acquire the data while a truck moves the bundle 600 through the perpendicular laser capture plane. The bundle 600 movement allows for the generation of cross-sections of the full length of the bundle 600. The amount of data acquired depends on the speed of the truck and the scanning frequency. The data may be organized in a Cartesian coordinate system CS=(X, Y, Z), following the convention shown in FIG. 5.

Figure 7:
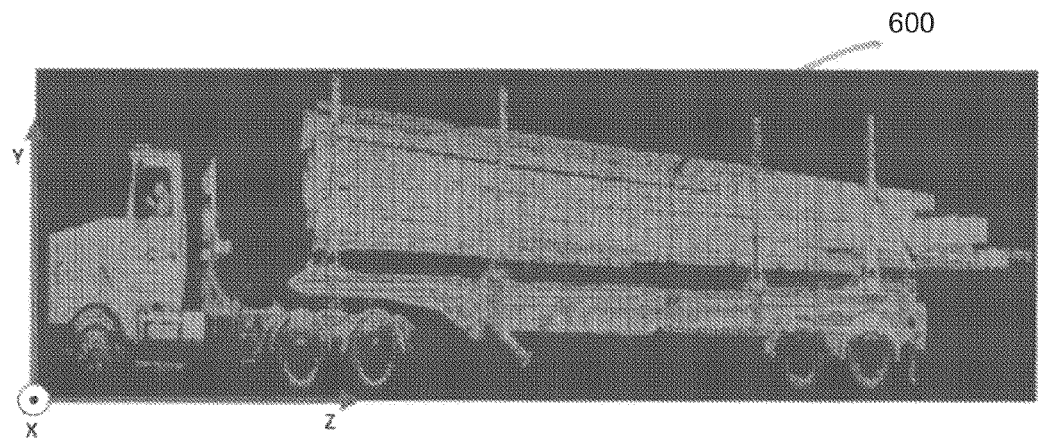

By combining the data acquired with a real-time measurement of the speed of the bundle 600, it is possible to reconstruct a three-dimensional image of the bundle 600 as shown in FIG. 6 (displayed in the Cartesian coordinate system in FIG. 7). The use of data from the diagonal lasers contributes to the generation of three-dimensional (3D) models with information on the back and/or front faces of the bundle 600 where all (or substantially all) of the logs 100 are exposed. The speed of the truck carrying the bundle 600 may be acquired through many means. One such method includes using an additional laser-scanner placed on the structure, either in a scanning plane parallel to the ground such that it scans the wheels of the vehicle or on top of the structure in a scanning plane parallel to the road and perpendicular to the ground such that it scans in a longitudinal way through the upper part of the truck, to measure the displacement and velocity of the truck by comparing and matching the shapes observed in subsequent scans. By identifying corresponding shapes in pairs of scans, and by determining the displacement vector between these corresponding shapes, the system is able to determine the truck's displacement between the time in which those scan were acquired. Another method includes using a radar speed measurement system placed in front of the truck, e.g., at a distance of at least one truck-length, to measure the change in position of the front of the truck over time. Other known methods for detecting the speed of moving objects may also be used. The acquired data may be provided to and stored in the first module 308 for further processing.

Figure 8:
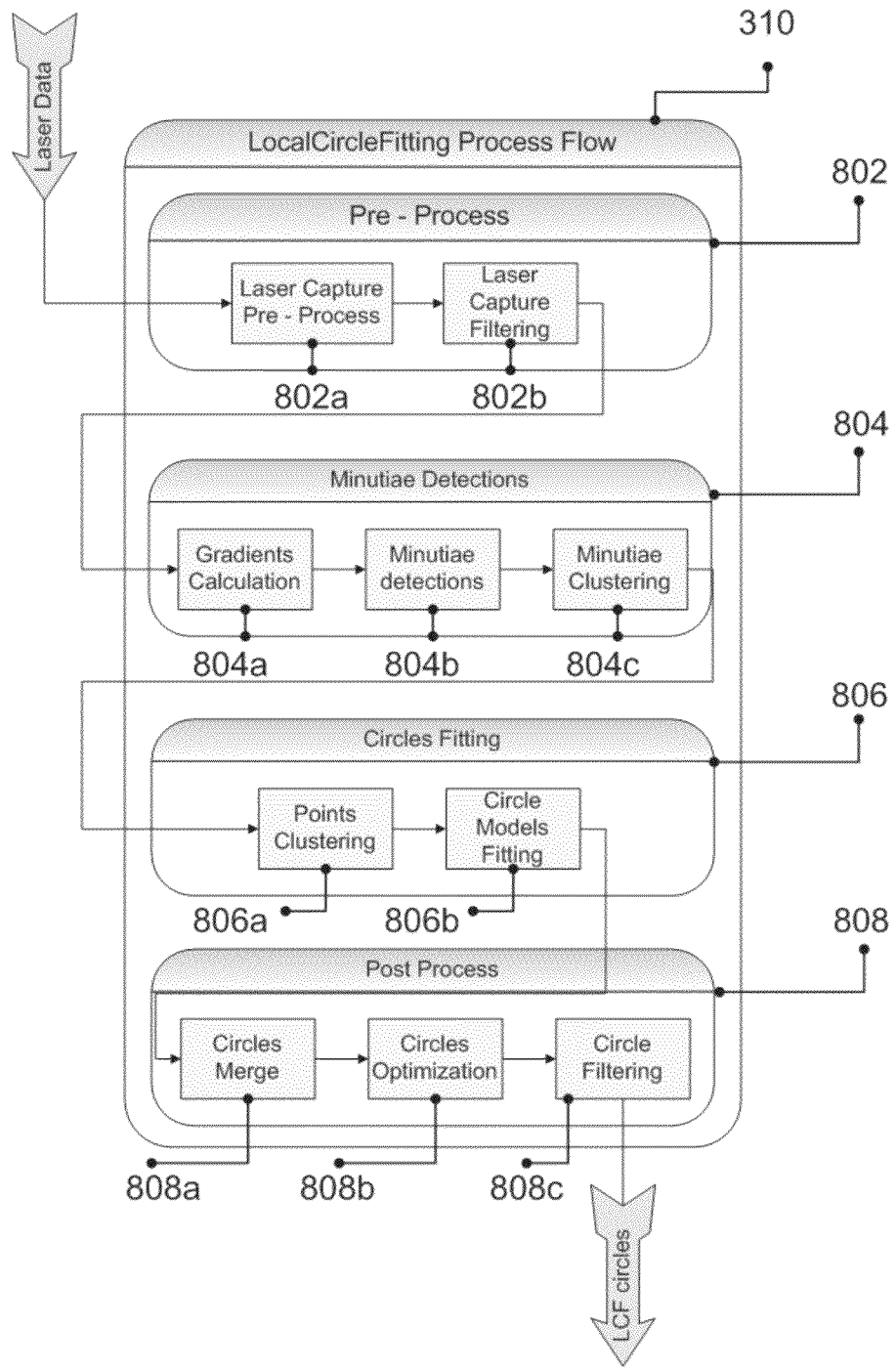
FIG. 8 is a block diagram illustrating by example a local circle fitting module according to an embodiment of the invention.

Following (or in some embodiments concurrent with) data acquisition (Step 202), the processor 304 executes the instructions in the second module 310 in the memory 306 to apply a curve fitting to find the best fitting shapes for the cross-section 500 of the logs 100 in the bundle 600, such as that depicted in FIG. 5 based on the perimeter of the logs 100, so that each shape represents a cross-section of an individual log 100. In some embodiments, the curve fitting technique is a local circle fitting technique. FIG. 8 depicts the module 310 adapted for fitting shapes (e.g., circles) to the cross-section 500. The module 310 includes modules for pre-processing the laser data (802) to sort and filter the acquired data, detecting minutiae (804) to locate special features, fitting circles (806) to fit groups of data to a circle model, and post-processing the circle models (808) by merging and filtering the generated circles and minimizing overlap between them. The module 310 may be executed for each laser scan independently.

The pre-process module 802 includes sorting the data points of each laser measurement (802a) to allow the system to make some assumptions about the order of angles. Often this is done in a clockwise manner. The pre-process module 802 also may include filtering out unreliable points of the laser measurements (802b) to eliminate poor quality data and to discard non-wood objects, such as load supports, wheels, load platform, driver cockpit, etc. Data filtering (802b) helps the entire local circle fitting module 310 proceed easier and faster, as well as produce better overall results. Data filtering (802b) may include applying one or more of the following filters: an amplitude filter to eliminate all the points that have lower amplitude than a given threshold; a Euclidean filter to eliminate isolated points of each scan by evaluating how many neighbors each point has within a determined maximum distance (all points that do not have the minimum required number of neighbors are filtered out of the data); an external window filter to eliminate all points outside of a determined rectangular window for each scan; and an internal window filter to eliminate all the points inside of a determined rectangular window for each scan.

Figure 9:
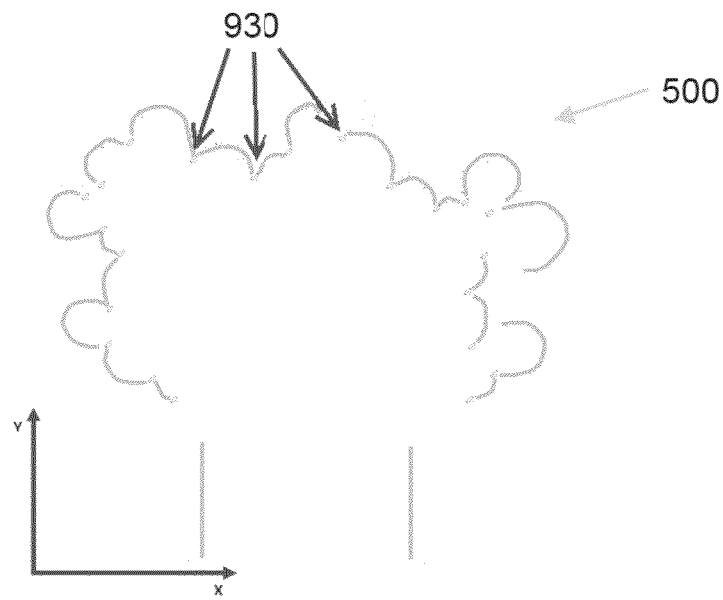
FIG. 9 depicts minutiae on a cross-section according to an embodiment of the invention.
Figure 10:
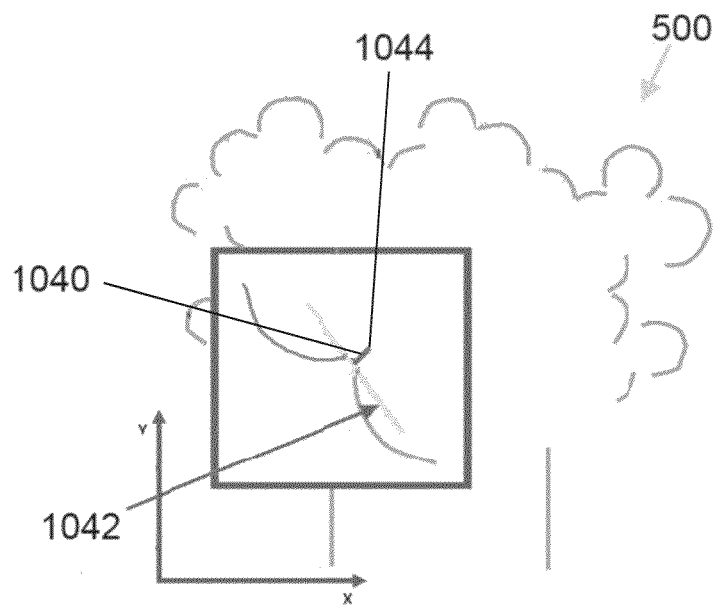
FIG. 10 depicts a method for determining minutia candidates according to an embodiment of the invention.

The minutiae detection module 804 detects special features, called minutiae, in each scan. A minutia may be the point where laser data of two contiguous logs intersect, as depicted by the points 930 in FIG. 9. Minutiae detection 804 includes generating candidates (804a), analyzing the candidates (804b), and clustering the minutiae (804c). During gradient calculation (804a), a set of minutiae candidates is generated by calculating gradients between consecutive points and forming a first minutiae group of points where the gradient exceeds a threshold. Other groups of points may be selected using a different rule, in some embodiments simultaneous with the other selections. For example, let $P_i=(X_i,Y_i)$ be the ith point 1040 measured by the laser sensor 420. To evaluate if the point $P_i$ 1040 belongs to a second set of minutiae candidates, the minutiae detection module 804 determines the line 1042 between the points $P_{i-n}$ and $P_{i+n}$, called $L_{i-n,i+n}$, where n is a parameter of the system, as depicted in FIG. 10. If the distance 1044 between $P_i$ and $L_{i-n,i+n}$ is higher than a fixed threshold, the point $P_i$ 1040 may be included in the second set of minutiae candidates. This module 804 may be executed as necessary for different threshold values.

Figure 11:
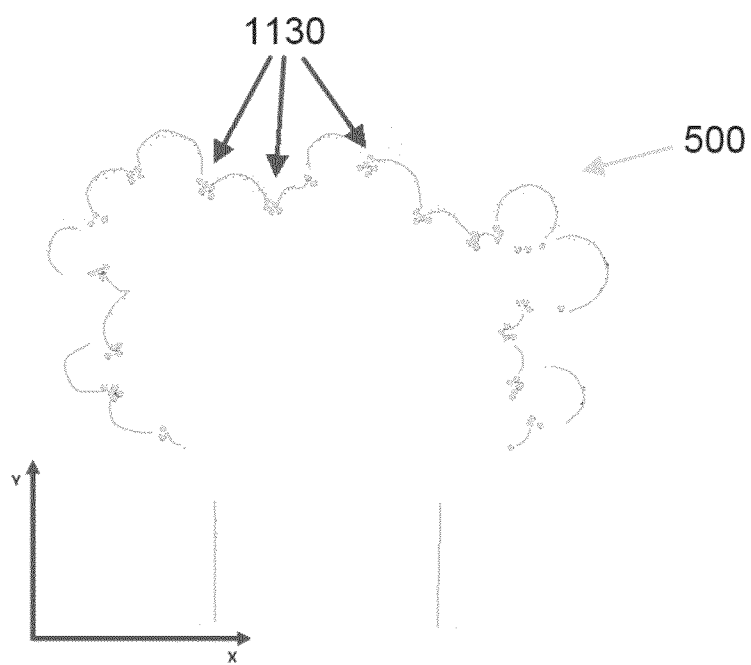
FIG. 11 depicts minutia clusters according to an embodiment of the invention.

Candidate analysis (804b), completed following determination of the candidates, involves determining a final set of minutiae that include the intersection between groups of candidates. During minutiae clustering (804c), the selected minutiae candidates 1130 depicted in FIG. 11 may appear to be grouped around the real minutiae. In one embodiment, a distance based clustering process may be executed over the set of minutia candidates 1130 to determine a unique minutia candidate for each real minutia. Those minutia candidates 1130 below a threshold value may be grouped, with the mean of each group serving as the final minutia.

The circle fitting module (806) may be executed to find circles that best fit the log data in each scan. Circular outlines may be generated from the data points of the previous steps through point clustering (806a) and circle model fitting (806b). Point clustering (806a) includes selecting groups of data points that are part of each log section by using an algorithm to select data points between two consecutive minutiae that indicate the selected data points pertain to a particular log 100. Circle model fitting (806b) follows selection of the points of each log section by executing an iterative circle-fitting algorithm to generate a circle mode. This procedure may be executed independently for each scan of each laser. The circle-fitting algorithm may have two stages: a first stage to create an initial circle approximation using standard least square circle fitting over the mentioned points; and a second stage to optimize the parameters of the circle obtained in the first stage by reducing the real distance of the points to the circle model. The iterative stage may provide a near-optimal result, however the post-processing module 808 may still be used.

The post-process module 808 includes merging circles (808a), optimizing circles (808b), and filtering circles (808c). The circles merge (808a) accounts for the overlapping circles generated by contiguous lasers that may be created as a result of the system detecting the same log section from independent laser scans. Each circle detection may be evaluated between the different lasers to determine if two circles are sufficiently overlapping, and if so, whether to merge them. In one exemplary embodiment, to evaluate if two circles are sufficiently overlapping, the post-processing module 808 calculates the common area of both circles. If this common area is above a certain threshold, the circles may be considered to be part of the same section and the points of both circles to be merged may be used to generate a new circle model using the circle-fitting algorithm of the circle model fitting (806b). This new estimation may improve both independent estimations because it uses more information to estimate the same circle.

Figure 12:
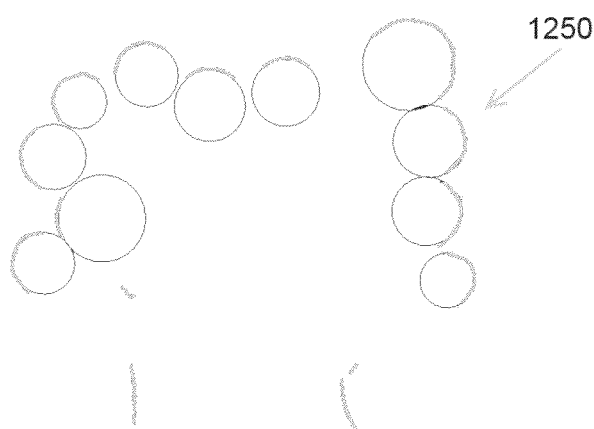
FIG. 12 depicts fitted circles according to an embodiment of the invention.

After circles are merged, the post-processing module 808 optimizes the merged circles by considering the overlap (calculated as the common area between each pair of circles) that can exist between circles of nearby model log sections. The circles should not overlap as the logs 100 do not overlap each other in the bundle 600. The optimization process (808b) seeks to minimize the total overlapped area between all circles in each scan, as well as the distance to the points of the laser to the circles models by adjusting the radius of each detected circle to create a final set of optimized circle detections. A gradient method that defines the optimal direction to move each radius to obtain a better fitness evaluation may be used. Finally, the post-processing module 808 filters out circles with diameters under or over set thresholds during circle filtering (808c), resulting in the circles 1250 depicted in FIG. 12. These thresholds may be based on real log diameter limits. In some embodiments, if the logs 100 are expected to have diameters of between approximately 10 and 50 inches, then the thresholds may be 9 and 55 inches. Different sizes of logs, both smaller and larger, may be used, and different threshold values may be used.

The second module 310 may also include additional instructions for processing the data from the diagonal lasers 302. One method may be based on peripheral trunk face (e.g., limits of the logs 100) detection. This method uses the detected circles 1250 given by the previous steps of the module 310 to generate several seeds near the respective trunk faces. Based on these seeds, an expectation maximization algorithm (EM) with a circular model dependent objective function may be developed to approximate the best circle near to the seeds which contains all the points of the data from the diagonal lasers 302 that describes a circular shape. This approximated circle may correspond to the face of a unique log 100, similar to how the circles 1250 relate to the other logs 100.

Other instructions may include bundling internal logs 100 by deleting data from the diagonal lasers 302 relating to peripheral logs 100. Using the remaining data from the diagonal lasers, the module 310 may detect faces of internal logs 100 using differences between laser scans. For example, if a difference with a high spatial density between information in consecutive scans is detected, a new seed may be generated, and the EM algorithm step may be developed based on the new seeds in the same way as in the peripheral case.

These instructions may supplement an existing model of the periphery loss to verify or correct the existing model. When there is not an existing model (e.g., for interior logs 100), a new model may be created based on the newly generated circles derived from the data from the diagonal lasers 302 (e.g., diameter information). In some embodiments, the data from the diagonal lasers 302 may help make the pre-existing circles more accurate.

Figure 13:
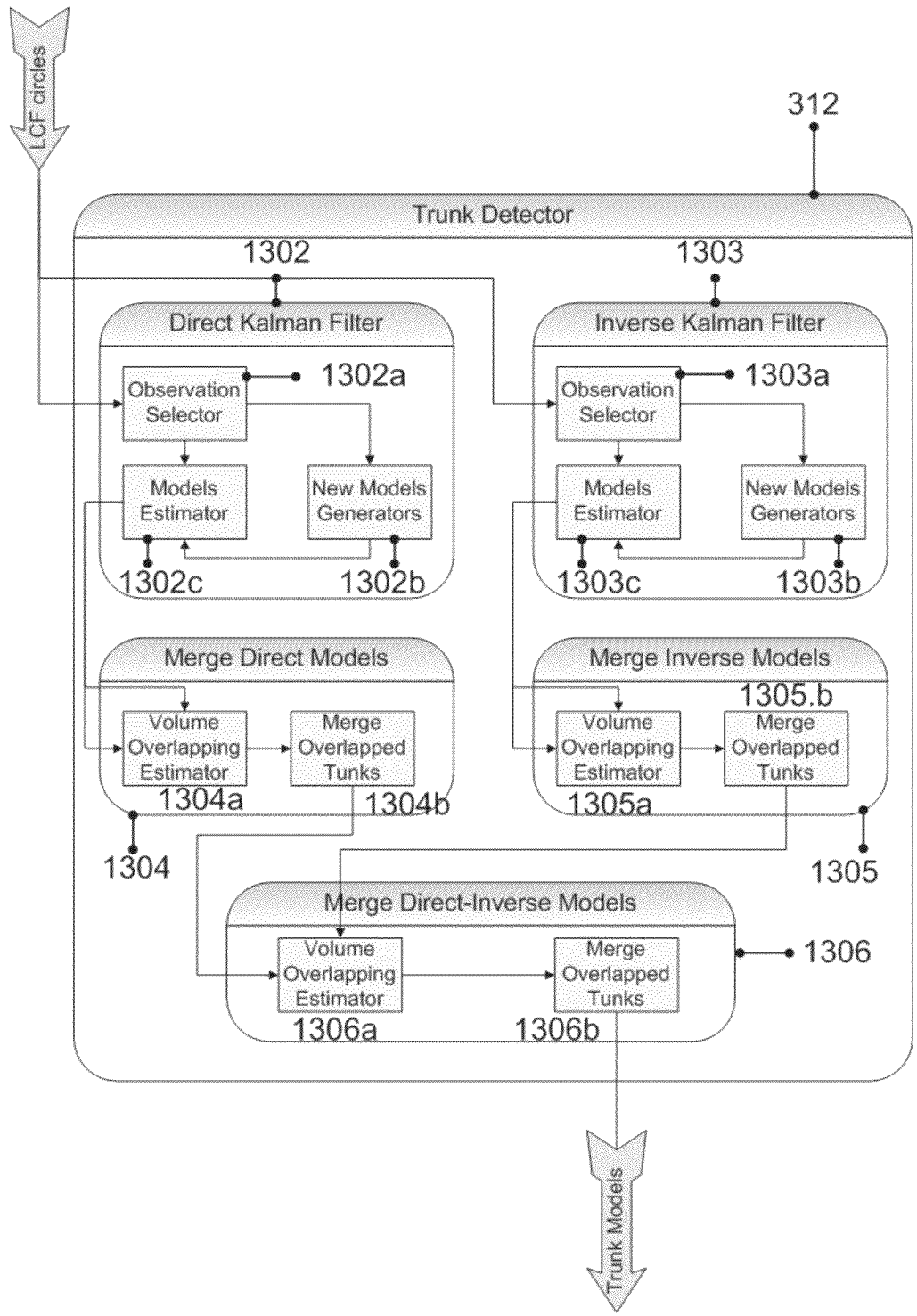
FIG. 13 is a block diagram illustrating by example a model creation module according to an embodiment of the invention.

The processor 304 may then execute the instructions in the third module 312 to estimate a model for each log 100 that is related to the fitted circles 1250, identifying groups of circles of the same log 100, and filtering the information to create a relatively smooth estimation of each log 100. FIG. 13 depicts the trunk detector/model creation module 312, which includes a direct Kalman filter 1302 and an inverse Kalman filter 1303 followed by modules for merging the direct models (1304) and merging the inverse models (1305), respectively, ending with a module for the merger of the direct and inverse models (1306).

The direct and inverse Kalman filters 1302/1303 are arranged in parallel, with one filter starting from the first scan of the bundle 600 and moving toward the last scan, and the other starting from the last scan working forward. This process aims to reduce the bias produced by the directionality of the Kalman filters 1302/1303 as direct and inverse filters often have different results due to the direction of the process. Each Kalman filter 1302/1303 has three stages, an observation selector 1302a/1303a, a new model generator 1302b/1303b, and a models estimator 1302c/1303c.

The observation selector 1302a/1303a evaluates if the circles 1250 of the current scan belong to any of the log models. Each circle 1250 may be compared with the existing models using the Mahalanobis distance. Additionally, a circle 1250 may be required to meet a confidence threshold given by the local circle fitting process 800 to be accepted as an observation. The circles 1250 that are near enough to a model and exceed the confidence threshold may be selected as observations of this model. The new model generators 1302b/1303b may consider whether the circles 1250 not associated with a model exceed a second confidence threshold to start a new log model. If not, the circles 1250 may be discarded. The models estimators 1302c/1303c include a standard Kalman filter that uses the position of the center of the log 100 and its radius in the current scan as the state of the model. Additionally, a velocity vector, which represents the direction in which the log diameter grows, may be estimated using the difference between observations of the log 100 in consecutive scans. This velocity value may be considered as the perturbation variable of the filtering process, and may be used to estimate the predictive state of the filtering. A corrective stage may be used to verify or modify the results, such as through a comparison with the circles 1250.

Once log models are generated by the Kalman filters 1302/1303, each log 100 may be represented by several separate models that need to be combined. During merge models (1304/1305), each model section may be compared to others to determine if they are part of the same log 100. Each merge model module 1304/1305 includes a volume overlapping estimator 1304a/1305a and a merge overlapped trunks module 1304b/1305b. The overlapping estimators 1304a/1305a compare pairs of log models to determine the overlapped volume between them in regions where the physical logs 100 are expected to be in contact. The overlapping estimators 1304a/1305a use an algorithm to make a cylindrical projection of the log to the scans where they could be overlapped. If the calculated overlapped volume exceeds a threshold volume ratio, the models may be merged by the merger modules 1304b/1305b. This process may be executed recursively, allowing more than two parts of a model log to be merged into the same model, and may be the same for both the direct and inverse Kalman Filter estimators 1302/1303.

The merge direct/inverse models module 1306 is used to merge the models generated by the estimators 1302/1303 to account for the directional bias using a volume overlapping estimator 1306a and a merge overlapped trunks module 1306b. The overlapping estimator 1306a may be similar to those described above (estimators 1304a/1305a) for use in calculating the volume overlap between log models. Those models exceeding the threshold may be designated for merger. The merge overlapped trunks module 1306b may consider those models designated to be merged and calculate a mean center and radius between the multiple models of the log 100. When the log 100 has only a single model associated with it, the merge module 1306b may simply select this model. In this manner, the merge module 1306b creates a final set of log models.

Figure 14A:
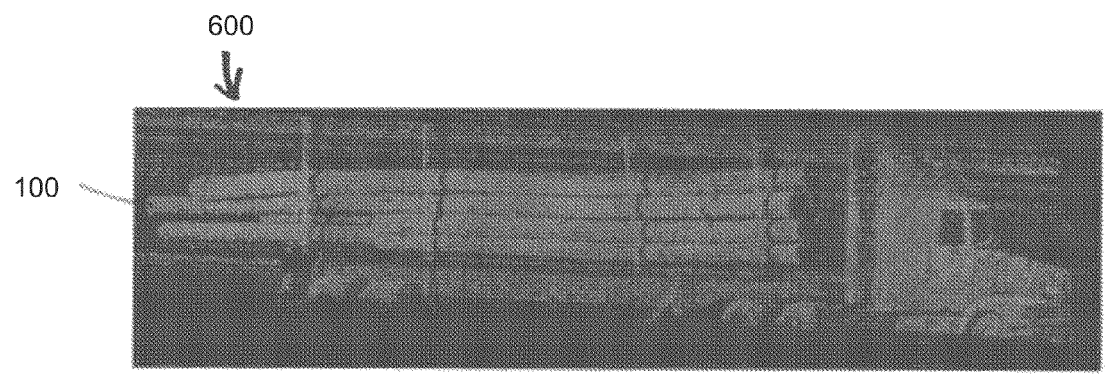
FIGS. 14A to 14C depict progression of model development according to an embodiment of the invention.
Figure 14B:
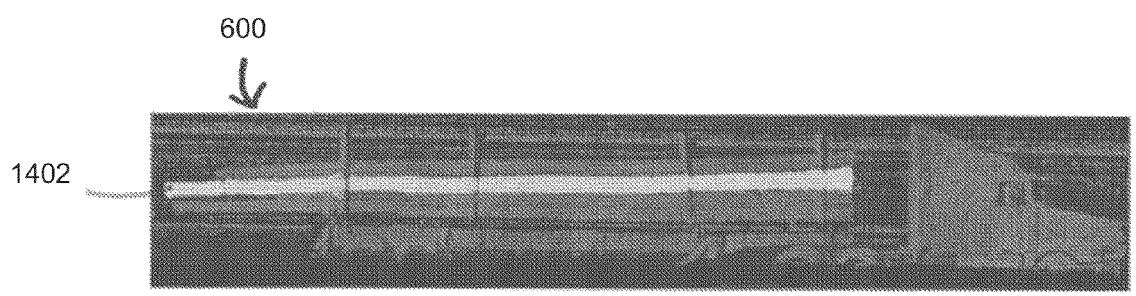
Figure 14C:
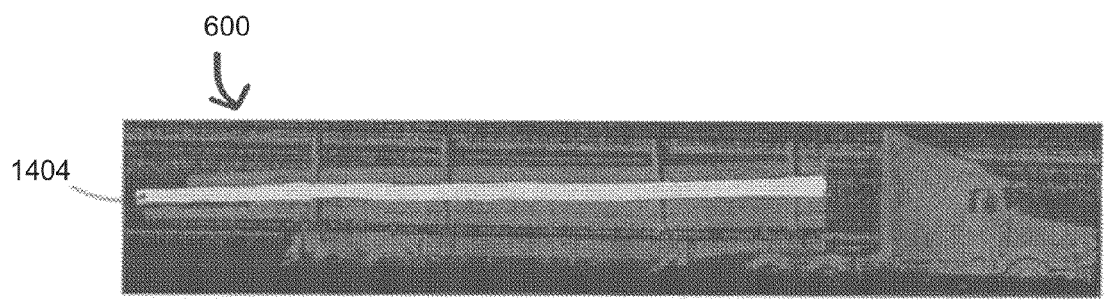

A progression of the model generation for a single log 100 is depicted in FIGS. 14A to 14C. FIG. 14A depicts a right side of the bundle 600 of logs 100 as scanned by the laser array 302. FIG. 14B depicts the associated observations (a series of circles) 1402 of a singular log 100 as estimated by one of the observation selector modules 1302a/1303a. FIG. 14C depicts the final model 1404 of the log 100 following filtering and completion of the last merge overlapped trunks module 1306b. The impact of the Kalman filters 1302/1303 can be seen in the differences between FIGS. 14B and 14C, including: i) generation of a filtered output, reducing the high frequencies of the changes between observations observed in FIG. 14B and ii) generation of a complete log model 1404 even where the log has no laser observations (e.g., near the vertical support bars that hold the load in place which produce a "shadow" in FIG. 14B as the laser scanners cannot see through them).

In certain embodiments, the process 200 optionally includes estimating confidence in the models 1404 (Step 208) for reliably detecting the distinguishing characteristics (e.g., length, small end diameter, large end diameter, curvature, etc.) to avoid false positive detections of defects. The estimating step (Step 208) also includes evaluating the data quality to dynamically define the best thresholds over the confidence values to discard or accept a measurement. The second module 310 may include instructions for determining an estimated detectable portion of a singular log 100, comparing the estimated detectable portion to the physical dimensional data associated with the log 100, and determining an occlusion factor based on the comparison. These instructions may be executed in conjunction with, or separate from, other instructions in the second module 310 for determining an intersection of a log 100 with another log 100 in the bundle 600. The second module 310 may be used estimate the visual region of each log from each laser sensor 302 by multiple methods. One method includes using real data to count the data points given by the lasers 420 for each log 100 and comparing this count with a section of the bundle perimeter the laser 420 was expected to have viewed (may be done for each log). Another method involves using a theoretical model that models all logs as cylinders and estimates the portion of the cylinder that should have been viewed by the laser 420 considering the occlusions generated by all the cylindrical logs. Both methods generate a measurement of the viewed and occluded regions of each log section for each complete log 100 over the entire bundle.

Data quality may be determined as a proportional factor of the difference between measurements obtained by these methods. If the difference in both measurements increases, it is likely more points that should be visible are not being seen, therefore lowering the data quality. This occlusion factor may be used to dynamically adjust some thresholds to filter out defects in undetected logs.

For each log 100, it may be desirable to know how much occlusion occurs where the system believes the large and small ends of the log 100 are located. If there is a high level of occlusion, the system may be less confident in determining the measurements of the distinguishing characteristics. To determine the level of occlusion, five occlusion factors may be calculated, with the first four relating to the level of occlusion in the scans just before and just after each end of the log 100, and the last one looking at occlusion for the entire log. With these occlusion factors, and using the dynamically estimated thresholds of data quality, the system may decide if each distinguishing characteristic can be calculated with the required confidence.

Analyzing the model (Step 210) is the final stage for estimating the distinguishing characteristics of each log 100. The relevant distinguishing characteristics of each log 100 may be measured from its associated model 1404, and the occlusion factors and data quality may be used to determine the confidence of these measurements. This confidence may be used to determine whether each measurement is indicative of the log 100 having a defect. The process 200 may help minimize the number of false positive defects calculated by the system while at the same time maximizing the number of true positives. The sensitivity of the system to calculating false positives can be adjusted according to the requirements of each mill, even for individual bundles 600.

Figure 15:
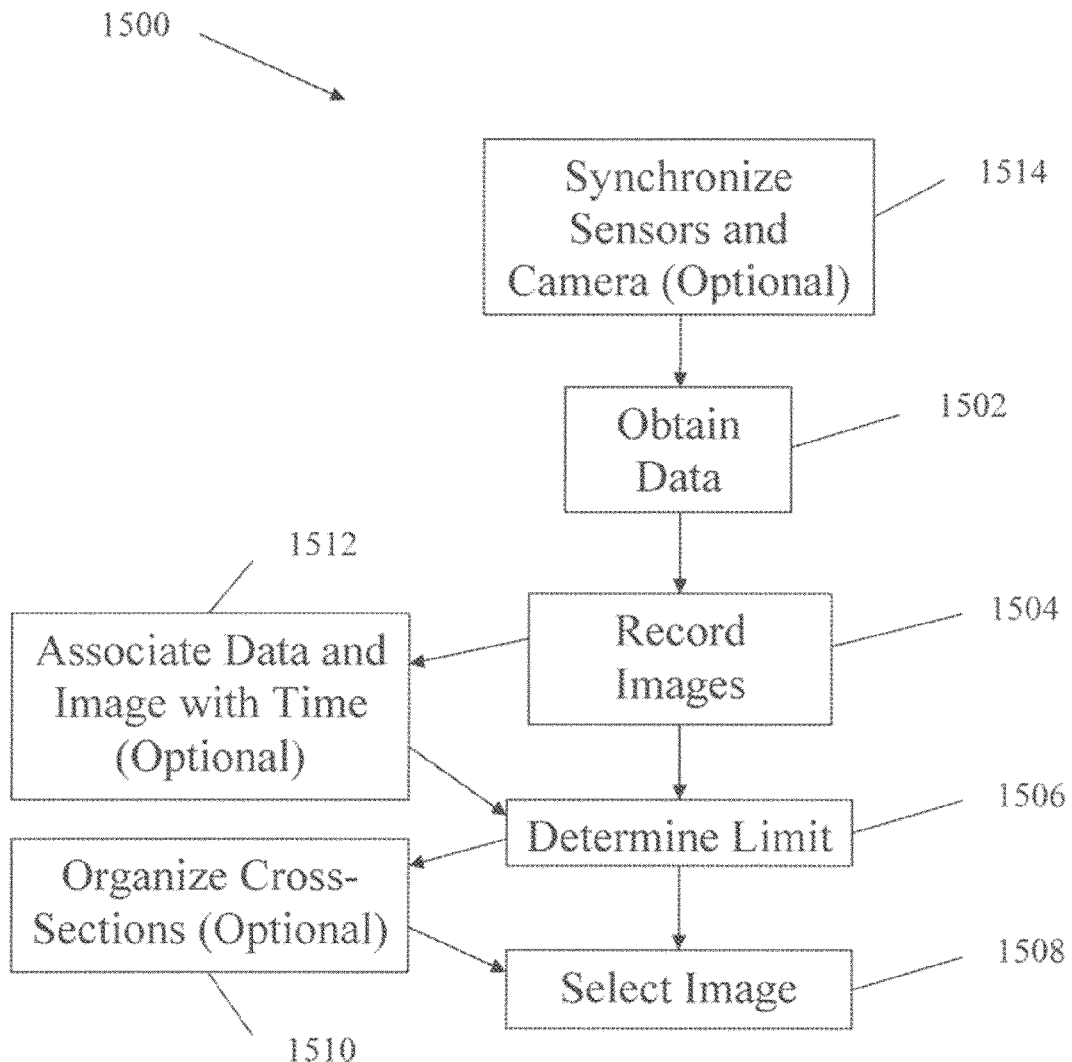
FIG. 15 is a block diagram illustrating by example a process for selecting images of a bundle of objects according to an embodiment of the invention.

FIG. 15 depicts another embodiment including a process 1500 directed to selecting an image of bundled objects. The process 1500 includes obtaining physical dimensional data about the bundle 600 (Step 1502), recording a plurality of images of the bundle 600 with at least one camera (Step 1504), processing the physical dimensional data with a processor to determine a limit of the bundle 600 (Step 1506), and selecting at least one image from the plurality of images corresponding to the limit (Step 1508). The process 1500 optionally includes organizing the data into a plurality of cross-sections of the bundle 600 (Step 1510), associating the data and at least one image with a common time indicator (Step 1512), and/or synchronizing the start of the sensors 302 and the camera with an electrical signal (Step 1514).

Figure 16:
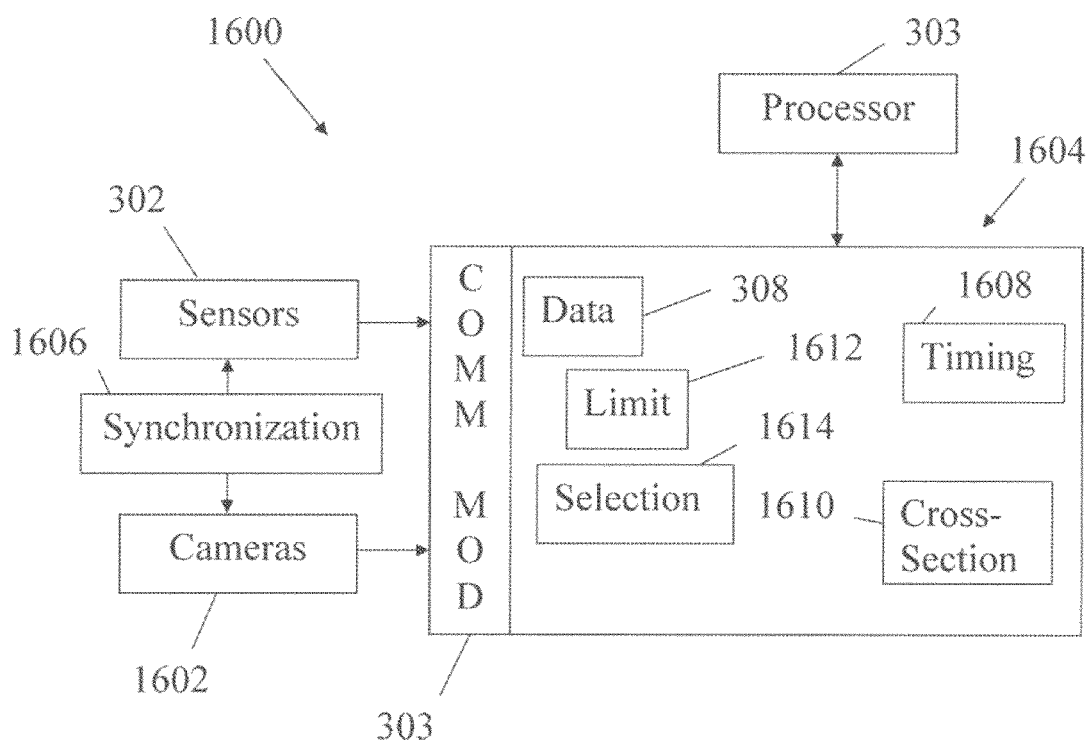
FIG. 16 is a block diagram illustrating by example a system for selecting images of a bundle of objects according to an embodiment of the invention.
Figure 17A:
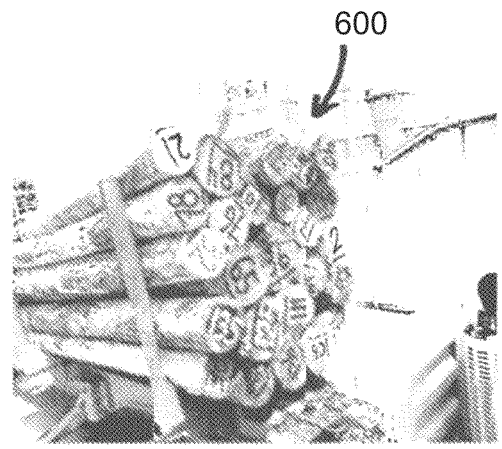
FIGS. 17A and 17B depict images of limits of a bundle according to an embodiment of the invention.
Figure 17B:
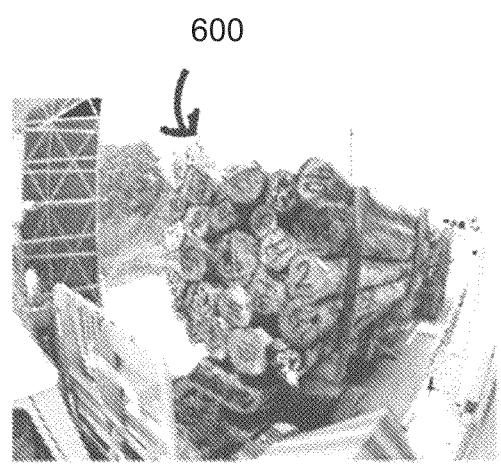

FIG. 16 depicts a related system 1600 for selecting images of bundled objects. The system 1600 includes the sensors 302 to obtain physical dimensional data about the bundle 600 as described above. Cameras 1602 are included in the system 1600 to obtain a plurality of images of the bundle 600. The cameras 1602 may be positioned on the structure 422, or may be located remote from the structure 422. The cameras 1602 may record video from which single images may be taken, or the camera 1602 may take photographs, at a high resolution while the bundle 600 moves through the structure 422. The cameras 1602 may be positioned and angled (e.g., similar to the lasers 302 in FIG. 4B) so that images of the front and back of the bundle 600, as well as the right and left-hand sides can be obtained. This setup may be extended to include cameras 1602 that capture the top and/or bottom side of the bundle 600. Using cameras 1602 with a high enough frame rate, detailed information of each part of the bundle 600 may be captured as can be seen in FIGS. 17A and 17B. The cumulative data 308 may be stored in memory/subsystem 1604, along with other modules.

Figure 18A:
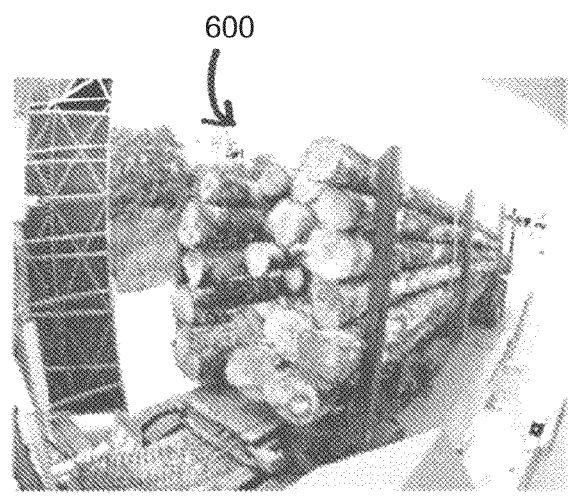
FIGS. 18A and 18B depict an image of a limit of a bundle and an associated scan according to an embodiment of the invention.
Figure 18B:
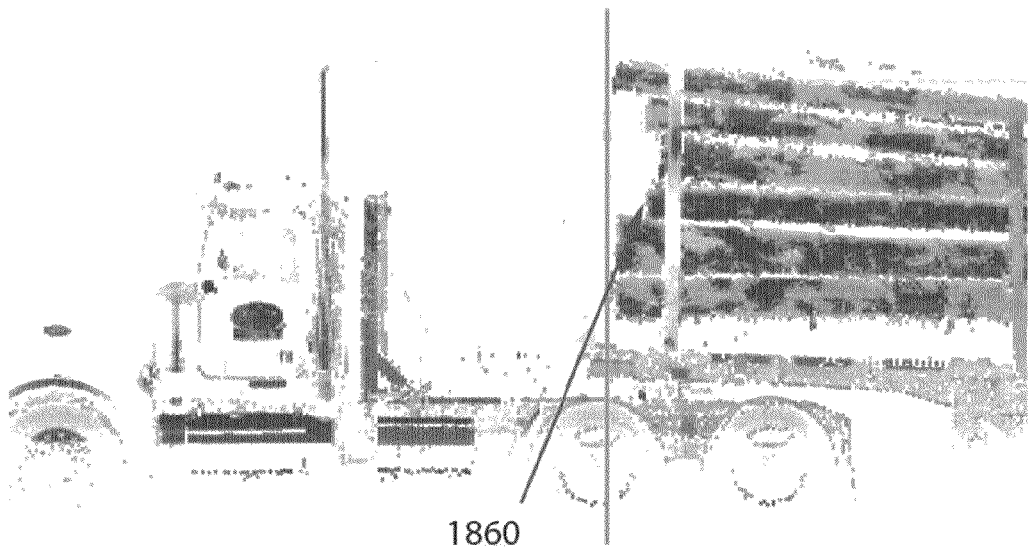

To synchronize the physical dimensional data from the sensors 302 with the image data from the cameras 1602, the scan rate of the sensors 302 and the frame rate of the cameras 1602 may be kept constant to ensure both sources of data remain synchronized. A synchronization mechanism 1606 may be used to help ensure the sensors 302 and the cameras 1602 begin operation at the same time. The synchronization mechanism 1606 may provide an electrical signal at a designated time (e.g., when the bundle 600 passes a certain point) to start the sensors 302 and the cameras 1602. When the rates are synchronized, each scan may be associated with a particular image. A timing module 1608 may be used to associate the physical dimensional data with at least one image, e.g., by associating a unique image (FIG. 18A) with a particular scan line 1860 (FIG. 18B). Additionally, a cross-section module 1610 may be used to organize the data into a plurality of cross-sections of the bundle 600. As each cross-section may have an associated image, it is possible to look at an image of the bundle 600 anywhere there is a detected cross-section.

Figure 19A:
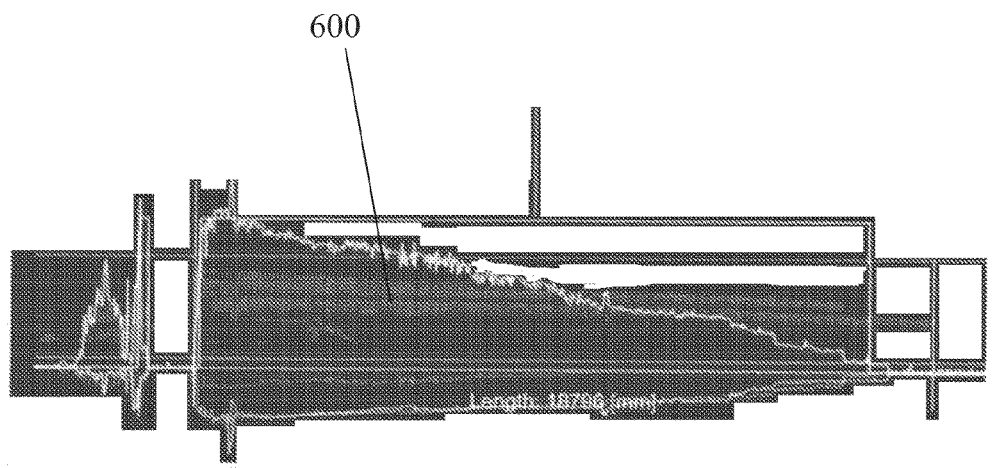
FIGS. 19A and 19B depict histograms of bundles according to an embodiment of the invention.
Figure 19B:
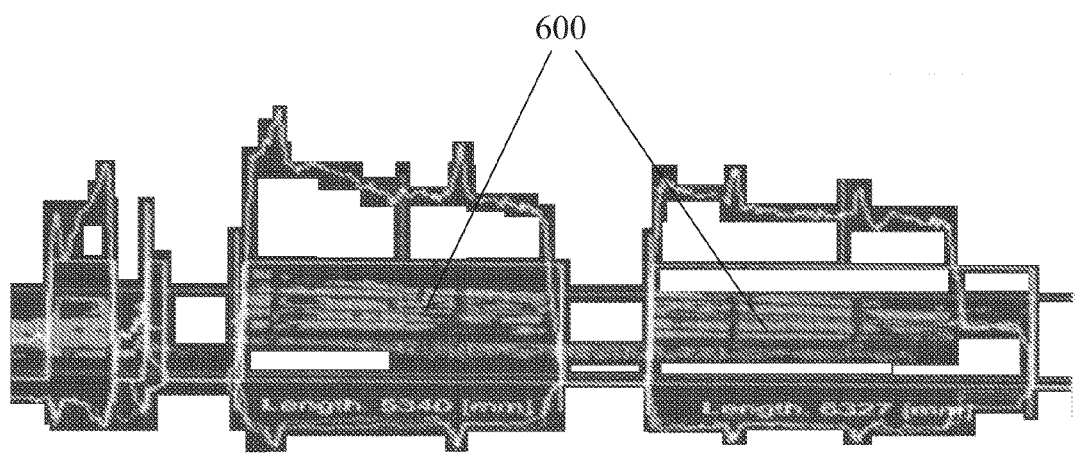

The images of greatest interest may be those of the limits or ends of the bundle. These limit images may enable a human user to perform a visual analysis to determine if a distinguishing characteristic is present (e.g., a swollen butt, a split, an uneven butt, etc.). To detect a limit of the bundle, the physical dimensional data may be processed according to the limit selection module 1612 by using a y-axis histogram calculation process, a bundle center calculation process, a bundle limits calculation, and a validation process. The y-axis histogram calculation process includes counting those data points located above a y-axis threshold. Exemplary histogram analyses are depicted in FIGS. 19A (single bundle 600) and 19B (multiple bundles 600). Multiple thresholds may be used, including one to find the initial scan of the bundle 600 and another to determine the final scan of the bundle 600. The bundle center calculation process may include processing y-axis histogram vectors to determine each bundle's central or middle scan. The bundle limits calculation process may include processing the y-axis histogram vectors starting at the determined center and working outwards. This process tends to result in limit detection with greater accuracy than existing methods. To validate the limit results, a number of rules may be applied, including the following: limits of different bundles 600 cannot overlap; the scan that marks the beginning of the load cannot come after the one that marks the end; and the limits of the load cannot be less than a certain distance or more than a certain distance apart (the distance used may vary based on application). Through this process, the limit module 1612 determines the limits of the bundle 600.

As the images are correlated with the laser scan data through the synchronization process described above, a selection module 1614 can automatically select at least one image from a plurality of images corresponding approximately to the limit. The selection module 1614 may select multiple images as others around the limit may provide a better view. For each bundle 600, several different images that show the front or back of the bundle 600 may be appropriate (the number can depend on factors such as truck speed, the camera frame rate, and the spacing between bundles). Images taken closer to the limit of the bundle 600 may allow an operator to view some logs 100 in greater detail (due to greater magnification), but can provide a more tangential angle of view to the log faces, thus making some logs 100 more difficult to view. Images taken from further away may provide a better angle of view, but can compromise the visible detail in each log 100. Often the optimum image may be considered to be the one where the operator has the best overall perspective of the front or end of the bundle 600 so as to visually determine defects (particularly those typically detected with a visual inspection, including swollen butts, splits, and uneven butts). The selection module 1614 may also be used to select images on either side of the optimum, accounting for other factors such as the speed of the bundle 600 through the structure 422, thus allowing the operator to scroll through different images in order to determine the best for visual inspection according to his/her subjective evaluation. Further, the selection module may select images from both limits so that the front and back ends of each bundle are displayed.

Figure 20:
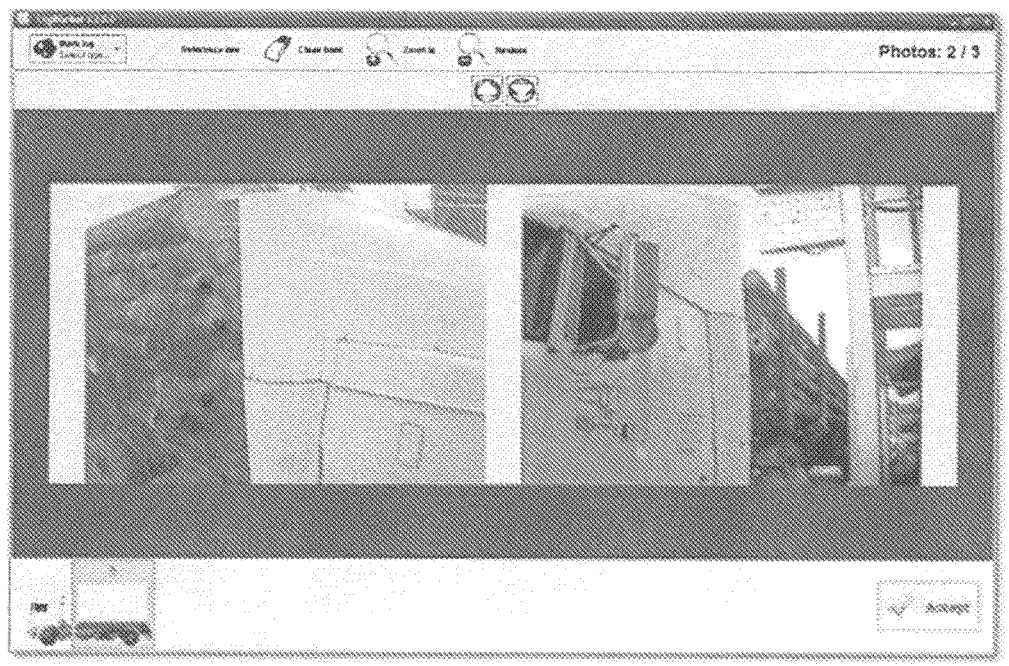
FIG. 20 depicts an interface for observing and marking images of bundles according to an embodiment of the invention.

The various images may be displayed in a user-friendly interface to help operators identify and mark log defects. This software may enable a user to easily scroll between different images if one automatically selected by the system is not ideal or if the operator desires a different viewing angle. Other features include the ability to adjust the color, contrast, white balance and other settings to compensate for problems with an image, such as poor lighting, the ability to zoom in and out of the image to focus on different details, and tools to digitally mark and color-code defects. An exemplary interface is depicted in FIG. 20.

The system allows an operator to conduct the visual inspection remote from the bundle 600 on a computer screen. This can help save time by eliminating the need for the operator to walk around, and in some cases even onto, the bundle 600. The operator may be located in an entirely different geographical location from the bundle 600, and multiple operators from various geographically distributed sites may analyze the images concurrently or at different times. Further, the bundle 600 may remain in motion while the data is acquired and the operator performs a visual analysis, or the images may be archived for later analysis. The system provides a location and time independent means for inspecting bundles 600 of logs 100, creating many efficiencies over the common current protocol.

Figure 21:
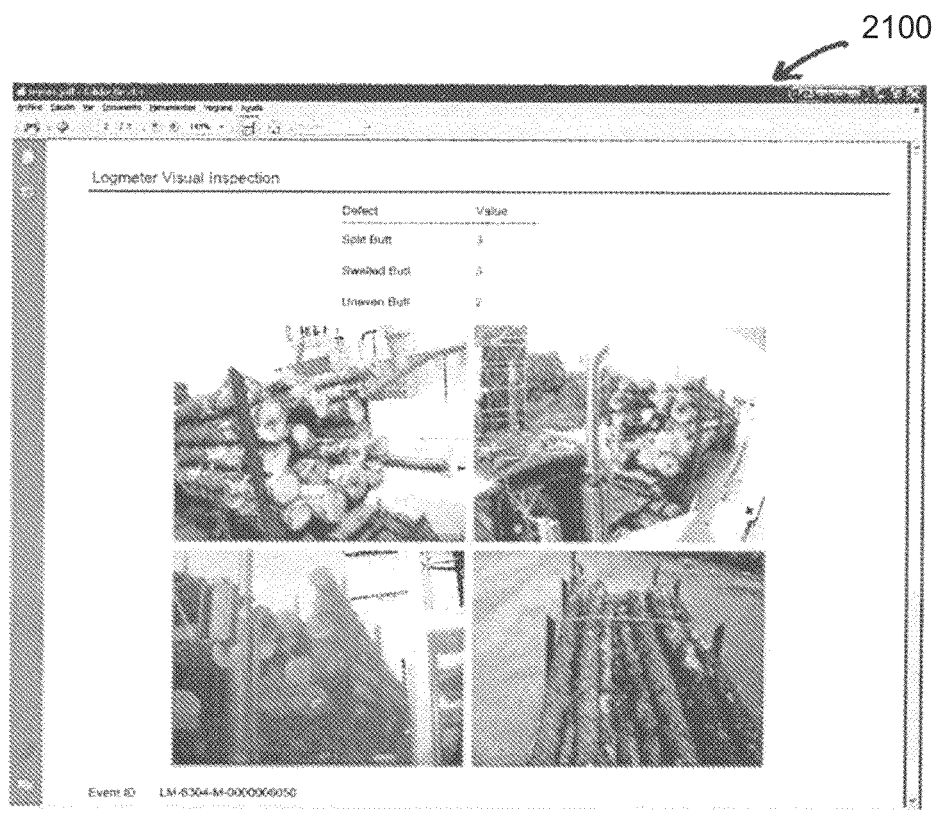
FIG. 21 depicts a report on a bundle according to an embodiment of the invention.

Often, it is desirable to generate a report of the measurements and observations. The response format may be adjusted for different applications, but generally includes a summary of the defects detected and a set of images illustrating the defects. FIG. 21 depicts one such report 2100, though the report 2100 may take many different forms. In many instances it is also desirable to inform the location's administrative or enterprise resource planning system so that the necessary actions can be taken, e.g., applying a discount to a dollar value of the bundle or adjusting a mill's inventory.

The information generated throughout the process, including the selected images and digital markings made by the human operator, may be stored for later review in an auditing system. Interested parties may later review the digital markings for a variety of reasons, including to determine the effectiveness of operators in detecting defects and to settle disputes with suppliers. The information may be referenced as long as the data is stored and accessible.

Although the exemplary operations described above recite steps performed in a particular order, the present invention does not necessarily need to operate in the recited order. One of ordinary skill in the art would recognize many variations, including performing steps in a different order.

Various embodiments and features of the present invention have been described in detail with particularity. The utilities thereof can be appreciated by those skilled in the art. It should be emphasized that the above-described embodiments of the present invention merely describe certain examples implementing the invention, including the best mode, in order to set forth a clear understanding of the principles of the invention. Numerous changes, variations, and modifications can be made to the embodiments described herein and the underlying concepts, without departing from the spirit and scope of the principles of the invention. All such variations and modifications are intended to be included within the scope of the present invention, as set forth herein. The scope of the present invention is to be defined by the claims, rather than limited by the forgoing description of various preferred and alternative embodiments. Accordingly, what is desired to be secured by Letters Patent is the invention as defined and differentiated in the claims, and all equivalents.

Computer Implementation

The algorithms and processing techniques described above may be implemented in software modules or hardware components that perform certain tasks. The algorithms and processing techniques may advantageously be configured to reside on an addressable storage medium and be configured to execute on one or more processors. The algorithms and processing techniques may be fully or partially implemented with a general purpose integrated circuit (IC), co-processor, FPGA, or ASIC. Thus, algorithms and processing technique may include, by way of example, components, such as software components, object-oriented software components, class libraries, class components and task components, processes, functions, attributes, procedures, subroutines, segments of program code, drivers, firmware, microcode, circuitry, data, databases, data structures, tables, arrays, and variables. The functionality provided for in the components and algorithms and processing techniques may be combined into fewer components and algorithms and processing techniques or further separated into additional components and algorithms and processing techniques. Additionally, the components and algorithms and processing techniques may advantageously be implemented on many different platforms, including computers, computer servers, data communications infrastructure equipment such as application-enabled switches or routers, or telecommunications infrastructure equipment, such as public or private telephone switches or private branch exchanges (PBX). In any of these cases, implementation may be achieved either by writing applications that are native to the chosen platform, or by interfacing the platform to one or more external application engines, for example, locally or over a network.

What is claimed is:

1. A bundled object image selection system, the system comprising:
    an array of sensors configured to at least partially surround a bundle of objects, wherein the sensors comprise lasers adapted to obtain physical dimensional data about the bundle;
    at least one camera configured to obtain a plurality of images of the bundle;
    a processor for executing computer-executable instructions; and
    a memory for storing computer executable instructions, that when executed by the processor implements (i) a limit module that processes the physical dimensional data to determine a limit of the bundle, wherein the limit module processes histogram vectors starting at a center of the bundle and working outwards and (ii) a selection module that selects at least one image from the plurality of images corresponding to the limit.

2. The system of claim 1, wherein the sensors are disposed on at least three sides of the bundle.

3. The system of claim 1, wherein the objects are logs.

4. The system of claim 1, wherein the physical dimensional data comprises distance and angle data between a plurality of set points.

5. The system of claim 1, wherein the camera is configured to take at least one of photographs and video.

6. The system of claim 1, wherein the selected image depicts an end of the bundle.

7. The system of claim 1 further comprising a cross-section module that organizes the physical dimensional data into a plurality of cross-sections of the bundle.

8. The system of claim 1 further comprising a timing module that associates the physical dimensional data with at least one image.

9. The system of claim 1 further comprising a synchronization mechanism.

10. The system of claim 9, wherein the synchronization mechanism is configured to use electrical signals to trigger the start of the sensors and the at least one camera.

11. A method for selecting an image of bundled objects, the method comprising:
    obtaining physical dimensional data about the bundled objects using laser sensors;
    recording a plurality of images of the bundled objects with at least one camera;
    processing the physical dimensional data with a processor to determine a limit of the bundle, wherein the processing comprises processing histogram vectors starting at a center of the bundle and working outwards; and
    selecting at least one image from the plurality of images corresponding to the limit.

12. The method of claim 11, wherein the obtaining step occurs when the objects are in relative motion to the laser sensors.

13. The method of claim 11, wherein the sensors are disposed on at least three sides of the bundle.

14. The method of claim 11, wherein the objects are logs.

15. The method of claim 11, wherein the physical dimensional data comprises distance and angle data between a plurality of set points.

16. The method of claim 11, wherein the recording step comprises taking one of photographs and video.

17. The method of claim 11, wherein the selected image depicts an end of the bundle.

18. The method of claim 11 further comprising the step of organizing the physical dimensional data into a plurality of cross-sections of the bundle.

19. The method of claim 11 further comprising the step of associating the physical dimensional data and the at least one image with a common time indicator.

20. The method of claim 11 further comprising synchronizing the start of the sensors and the at least one camera with an electrical signal.

* * * * *